(12) United States Patent
Walker et al.

(10) Patent No.: US 6,470,200 B2
(45) Date of Patent: Oct. 22, 2002

(54) PACIFIER PULSE OXIMETER SENSOR

(75) Inventors: Steven C. Walker, Baldwin, MO (US);
John G. Alexander, O'Fallon, IL (US);
John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 52 days.

(21) Appl. No.: 09/780,570

(22) Filed: Feb. 12, 2001

(65) Prior Publication Data

US 2001/0029324 A1 Oct. 11, 2001

Related U.S. Application Data

(60) Provisional application No. 60/182,018, filed on Feb. 11, 2000.

(51) Int. Cl.$^7$ .................................................. A61B 5/00
(52) U.S. Cl. ......................................... 600/344; 600/323
(58) Field of Search ................................. 600/310, 322, 600/323, 340, 344

(56) References Cited

U.S. PATENT DOCUMENTS

| 2,669,988 A | 2/1954 | Carpenter |
| 2,882,893 A | 4/1959 | Godfroy |
| 3,908,665 A | 9/1975 | Moses |
| 4,112,936 A | 9/1978 | Blachly |
| 4,198,970 A | 4/1980 | Luomanen |
| 4,222,391 A | 9/1980 | Rawson et al. |
| 4,270,531 A | 6/1981 | Blachly et al. |
| 4,481,949 A | 11/1984 | Kesserling et al. |
| 4,495,945 A | 1/1985 | Liegner |
| 4,545,378 A | 10/1985 | Chrones |
| 4,586,513 A | 5/1986 | Hamaguri |
| 4,621,643 A | 11/1986 | New, Jr. et al. |
| 4,624,572 A | 11/1986 | Van Den Bosch .......... 356/418 |
| 4,651,746 A | 3/1987 | Wall |
| 4,676,240 A | 6/1987 | Gardy |
| 4,700,708 A | 10/1987 | New, Jr. et al. |
| 4,715,379 A | 12/1987 | McCormick |
| 4,796,636 A | 1/1989 | Branstetter et al. |
| 4,830,014 A | 5/1989 | Goodman et al. |
| 4,854,699 A | 8/1989 | Edgar, Jr. ..................... 356/41 |
| 4,859,057 A | 8/1989 | Taylor et al. .................. 356/41 |
| 4,865,038 A | 9/1989 | Rich et al. |
| 4,867,557 A | 9/1989 | Takatani et al. ............... 356/41 |
| 4,880,304 A | 11/1989 | Jaeb et al. ..................... 356/41 |

(List continued on next page.)

FOREIGN PATENT DOCUMENTS

| DE | 44 42 260 A1 | 5/1996 |
| FR | 2729842 A | 8/1996 |
| WO | WO 83/02664 | 8/1983 |

(List continued on next page.)

OTHER PUBLICATIONS

Anonymous, "Photon Flow For Pulse Oximetry," Sep. 15, 1995, Web. Article: HTTP://WWW.LLNL.GOV/BBRP/HEALTHCARE/PROJECTS/PFPULSEOXIM.html.

(List continued on next page.)

*Primary Examiner*—Eric F. Winakur
(74) *Attorney, Agent, or Firm*—Elizabeth Arwine

(57) ABSTRACT

A pacifier pulse oximeter sensor includes pulse oximeter sensor elements located within the nipple of a pacifier. The pulse oximeter sensor elements may be completely within the nipple material, embedded within the nipple material, nested within the nipple material, or adjacent to the nipple material while not being exposed to the outside environment. The pulse oximeter sensor elements include a light source and a light detector. The pulse oximeter sensor elements communicate with an oximeter through wiring, an electrical connector, and/or wirelessly. An alternative embodiment adds oximeter processing capabilities to the pacifier pulse oximeter sensor.

20 Claims, 6 Drawing Sheets

U.S. PATENT DOCUMENTS

| | | | |
|---|---|---|---|
| 4,890,619 A | 1/1990 | Hatschek | |
| 5,013,160 A | 5/1991 | Massey et al. | 374/151 |
| 5,040,539 A | 8/1991 | Schmitt et al. | |
| 5,069,214 A | 12/1991 | Samaras et al. | |
| 5,090,410 A | 2/1992 | Saper et al. | |
| 5,193,544 A | 3/1993 | Jaffe | |
| 5,197,875 A | 3/1993 | Nerli | 433/80 |
| 5,203,329 A | 4/1993 | Takatani et al. | |
| 5,205,281 A | 4/1993 | Buchanan | |
| 5,217,012 A | 6/1993 | Young et al. | |
| 5,226,417 A | 7/1993 | Swedlow et al. | |
| 5,246,003 A | 9/1993 | Delonzor | |
| 5,282,464 A | 2/1994 | Brain | |
| 5,292,336 A | 3/1994 | Spence, Jr. et al. | 606/236 |
| 5,318,017 A | 6/1994 | Ellison | |
| 5,329,922 A | 7/1994 | Atlee, III | |
| 5,337,744 A | 8/1994 | Branigan | |
| 5,355,874 A | 10/1994 | Bertram | |
| 5,357,954 A | 10/1994 | Shigezawa et al. | |
| 5,361,757 A | 11/1994 | Smith et al. | |
| 5,413,101 A | 5/1995 | Sugiura | |
| 5,417,207 A | 5/1995 | Young et al. | |
| 5,494,032 A | 2/1996 | Robinson et al. | |
| 5,595,176 A | 1/1997 | Yamaura | |
| 5,596,986 A | 1/1997 | Goldfarb | |
| 5,619,992 A | 4/1997 | Guthrie et al. | |
| 5,638,593 A | 6/1997 | Gerhardt et al. | 29/592.1 |
| 5,655,519 A | 8/1997 | Alfrey | |
| 5,673,693 A | 10/1997 | Solenberger | |
| 5,678,544 A | 10/1997 | Delonzor et al. | |
| 5,715,816 A | 2/1998 | Mainiero et al. | |
| 5,743,261 A | 4/1998 | Mainiero et al. | |
| 5,755,226 A | 5/1998 | Carim et al. | |
| 5,797,841 A | 8/1998 | Delonzor et al. | 600/323 |
| 5,800,349 A | 9/1998 | Isaacson et al. | 600/323 |
| 5,810,000 A | 9/1998 | Stevens | 128/200.26 |
| 5,817,009 A | 10/1998 | Rosenheimer et al. | 600/339 |
| 5,839,439 A | 11/1998 | Nierlich et al. | |
| 5,954,050 A | 9/1999 | Christopher | 128/204.23 |
| 5,983,120 A | 11/1999 | Groner et al. | 600/310 |
| 5,991,648 A | 11/1999 | Levin | 600/344 |
| 6,253,098 B1 | 6/2001 | Walker et al. | 600/344 |
| 6,256,524 B1 | 7/2001 | Walker et al. | 600/340 |
| 6,263,223 B1 | 7/2001 | Shepherd et al. | 600/340 |
| 6,266,547 B1 | 7/2001 | Walker et al. | 600/344 |
| 2002/0028990 A1 | 3/2002 | Shepherd et al. | |

FOREIGN PATENT DOCUMENTS

| | | |
|---|---|---|
| WO | WO 86/00207 | 1/1986 |
| WO | WO 90/01293 | 2/1990 |
| WO | WO 90/07907 | 7/1990 |
| WO | WO 96/29927 | 10/1996 |
| WO | WO 96/31155 | 10/1996 |
| WO | WO 97/42903 | 11/1997 |
| WO | WO 00/13567 | 3/2000 |
| WO | WO 00/13575 | 3/2000 |
| WO | WO 00/13576 | 3/2000 |
| WO | WO 00/13577 | 3/2000 |

OTHER PUBLICATIONS

Cote et al., "Tongue Oximetry in Children with Extensive Thermal Injury: Comparison with Peripheral Oximetry," Can. Journal Anaesth., 1992, vol. 39, Issue 5, pp. 454–457.

Faisst et al., "Intrapartum Reflectance Pulse Oximetry: Effects of Sensor Location and Fixation Duration on Oxygen Saturation Readings," Journal of Clinical Monitoring, Sep. 1997, vol. 13, No. 5, pp. 299–302.

Faisst et al., "Reflectance Pulse Oximetry in Neonates," European Journal of Obstetrics & Gynecology and Reproductive Biology, 1995, vol. 61, pp. 117–122.

Hayes et al., "Quantitative Investigation of Artefact in Photoplyethysmography and Pulse Oximetry for Respiratory Exercise Testing," printed Aug. 27, 1998, Web Article: HTTP://WWW.LUT.AC.UK/DEPARTMETNS/EL/RE-SEARCH/OPTICS/PPGRAPHY/PAPER2c.htm.

HealthGate Data Corp., "Pulse Oximetry," Jun. 13, 1997, Web Article: HTTP://WWW.HEALTHGATE.COM/HEALTHGATE/FREE/DPH/STATIC/DPH.0200.shtml.

Izumi et al., "Accuracy and Utility of a New Reflectance Pulse Oximeter for Fetal Monitoring During Labor," Journal of Clinical Monitoring, Mar. 1997, vol. 13, No. 2, pp. 103–108.

Jobes et al., "Monitoring of Arterial Hemoglobin Oxygen Saturation Using a Tongue Sensor," Anesthesia & Analgesia, 1998, vol. 67, pp. 186–188.

O'Leary et al., "Buccal Pulse Oximeter is More Accurate Than Finger Pulse Oximeter in Measuring Oxygen Saturation," Anesthesia & Analgesia, 1992, vol. 75, pp. 495–498.

Reynolds et al., "Influence of Sensor Site Location on Pulse Oximetry Kinetics in Children," Anesthesia & Analgesia, 1993, vol. 76, pp. 751–754.

Sheridan et al., "Intraoperative Reflectance Pulse Oximetry in Burn Patients," Journal of Clinical Monitoring, Jan. 1995, vol. 11, No. 1, pp. 32–24

Ogino et al., "Reflectance Pulse Oximeter Measuring Central $SaO_2$ From Mouth," Proceedings of the Annual International Conference of the IEEE Engineering in Medicine and Biology, Nov. 3, 1994, vol. 16, No. 3, pp. 914–915.

Guillermo E. Lema, "Oral Pulse Oximetry in Small Children," Anesthesia and Analgesia, Mar. 1991, vol. 27, No. 3, p. 414.

PACIFIER PULSE OXIMETER SENSOR

This application claims the benefit of U.S. provisional Application Serial No. 60/182,018, filed Feb. 11, 2000, entitled Pacifier with Reflectance Pulse Oximetry, which is hereby incorporated by reference.

I. FIELD OF THE INVENTION

This invention is directed to an apparatus and a method for measuring blood oxygenation from locations within the oral cavity of a subject, for example, a small child or a small/newborn animal. More particularly, the invention relates to using pulse oximeter sensors to perform reflective pulse oximetry within the oral cavity of a subject.

II. BACKGROUND OF THE INVENTION

With a few exceptions, tradition and technology have favored transillumination pulse oximetry in the operating theater. The principle of operation of the pulse oximeter is fairly simple but is arguably the most important development in anesthesia monitoring in the twentieth century. Two wavelengths of light (usually 660 nm and 940 nm) are used to spectrophotometrically determine the ratio of oxidized to reduced hemoglobin noninvasively as well as to determine the pulsatility of blood plethysmographically.

However, reflectance oximetry rather than transillumination oximetry was the earliest investigative form of the technique for taking oximeter readings. Transillumination pulse oximetry, without question, is the most effective form when oximetry is obtained through skin. However, when skin is not interposed as a barrier to capillary bed access, reflectance pulse oximetry easily can be achieved with very accurate results. Indeed, it is used commonly and effectively among intrapartum and neonatal patients whose capillary beds are easily accessed through their skin. The technique has also been applied to adult and pediatric burn patients by placing the reflectance sensor in wounds or over hyperemic sites such as healed partial thickness burns. The effect is achieved by the backscattering of incident bispectral light that traverses and, on reflection from nonabsorptive collagenous tissues, retraverses formed elements in the blood back to the oximeter elements. Rather than superseding transillumination pulse oximetry, this technique broadens the scope of possible monitoring sites, adding to the clinician's armamentarium.

Presently, the most common application of this in a medical setting is via transillumination through the capillary bed of a peripheral digit. However, young patients such as babies are apt to remove or reject foreign objects such as finger oximeters or inserted tubes upon realizing their placement when recovering from anesthesia or awaking from sleep. Sick children, in particular, are more likely to be restless and easily agitated and thus will resist any attempts to have medical readings taken like temperature or oximeter readings. Additionally, it is not unusual for multitrauma and thermally injured patients to either have severe peripheral vasoconstriction or to have severely damaged (or missing due to amputation) peripheral vascular beds.

There are other often overlooked capillary beds readily accessible in most adult burn patients and young children that are as amenable to reflectance oximetry similar to the forehead of the premature infant. The buccal surface, posterior soft palate, hard palate, lingual surfaces, and gums of a burned patient and/or child are seldom compromised no matter how severe the burn, and the capillary beds are very close to the surface in those areas. Transillumination pulse oximetry of the tongue and cheek has been documented as a viable method of monitoring, but not everyone has the equipment available to place a transilluminating pulse oximeter on the tongue or cheek.

Recent studies indicate that oral pulse oximetry is a superior modality when compared to peripheral transillumination pulse oximetry. A variety of studies have shown that oral pulse oximeters are more reliably and rapidly responsive than peripheral pulse oximeters. However, these studies use oral transillumination pulse oximetry, held in place via complex devices or pieces of improvised malleable metal. Oral secretions, equipment failure, and placement difficulty often render these techniques ineffective.

Prior pulse oximeter sensors inserted through the mouth are usable only when the patient is under general anesthesia. These pulse oximeter sensors are inserted to reach the larynx area, for example, U.S. Pat. No. 5,282,464 to Brain et al. Another known method uses transillumination pulse oximetry of the posterior tongue, but this method possibly may not be used with a patient, who is awake, for example, U.S. Pat. No. 5,205,281 to Buchanan. Also, the posterior tongue is not the most accessible body part to take oximetry measurements.

Notwithstanding the usefulness of the above-described devices, and the above-identified recognized viability of transilluminating pulse oximetry, a need exists for a more convenient method for obtaining oximeter readings from a subject.

III. SUMMARY OF THE INVENTION

The invention while addressing the problems of the prior art obtains advantages that were not achievable with the prior art apparatuses and methods.

An object of this invention is to provide an effective method for taking pulse oximetry measurements from oral capillary beds.

Another object of the invention is the use of reflectance pulse oximetry via the oral cavity for a variety of surgical, anesthetic, or critical care procedures or situations to include patients that are awake, undergoing general anesthesia, or recovering from general anesthesia.

Another object of the invention is to allow for lingual placement of a pulse oximeter sensor for reflectance readings to provide efficient and clinically accurate pulse oximetry measurements.

Another object of the invention is to allow for buccal placement of a pulse oximeter sensor for reflectance readings to provide efficient and clinically accurate pulse oximetry measurements.

Yet another object of the invention is to monitor oxygen levels in newborns and young children who are difficult to monitor because of their natural restlessness and young age.

Still another object of the invention is to monitor oxygen levels in severely burned ICU patients who are difficult to monitor.

An advantage of the invention is an improvement in the quality of care resulting from using a straightforward method with easily used devices to take internal oximetry measurements and readings.

Another advantage of the invention is that EMS crews and personnel will be able to use this invention easily in the field during, for example, emergency situations.

Another advantage of the invention is improved pulse oximetry readings.

Another advantage of the invention is reflectance pulse oximetry requires less power to function and thus less heat is produced than transilluminance pulse oximetry. The decrease in produced heat lowers the risk the subject will be burned.

Yet another advantage of the invention is that ambient light will not degrade the oximeter readings because the invention is within the mouth of a subject.

The apparatus and the method accomplish the above objectives and achieve the advantages. The apparatus and the method are easily adapted to a wide variety of situations.

Furthermore, intraoral buccal, palatal, or lingual placement of a pulse oximeter probe in a configuration relying upon reflected light will provide pulse oximetry measurements comparable to those obtained by peripheral pulse oximetry. Test protocols suggest that buccal and palatal reflectance pulse oximetry provides a simple, accurate means of monitoring arterial oxygen saturation in the severely burned patient where oximetric monitoring presents a challenge.

Furthermore, the apparatus to perform this method is extremely useful in cases where it is difficult at best or not even possible to attach prior art pulse oximeter sensors with clips or straps to the patient. The types of patients that this apparatus would be useful with are critically ill or injured patients including newborns, babies, young children, young animals, and burn or trauma patients without alternative sites and maxillofacial injuries.

Given the following enabling description of the drawings, the apparatus and the method should become evident to a person of ordinary skill in the art.

IV. DESCRIPTION OF THE DRAWINGS

The use of cross-hatching within these drawings should not be interpreted as a limitation on the potential materials used for construction. Like reference numerals in the figures represent and refer to the same element or function.

Figure 21A:
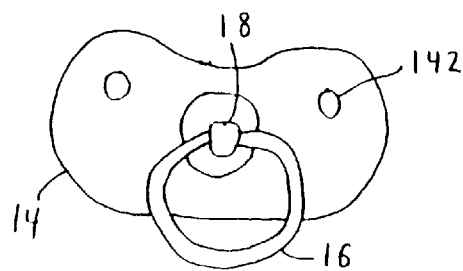
Figure 21B:
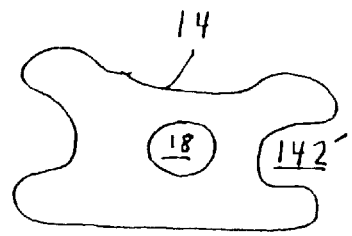

FIGS. 21(a)–(b) depict an example of a shield structure for use in the preferred embodiment of the invention.

Figure 22:
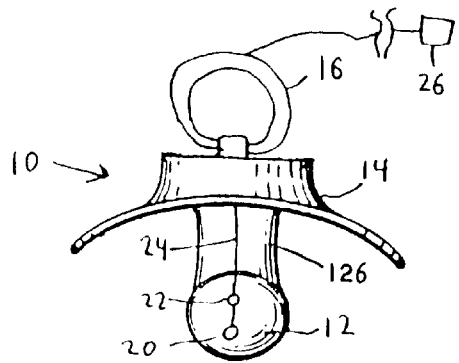

FIG. 22 illustrates a top view of an alternative embodiment of the invention.

Figure 23:
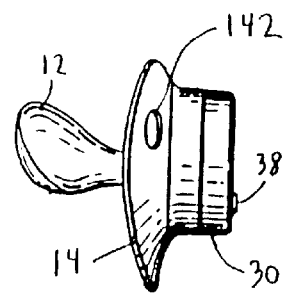

FIG. 23 depicts a top cross-section of another alternative embodiment of the invention.

Figure 24:
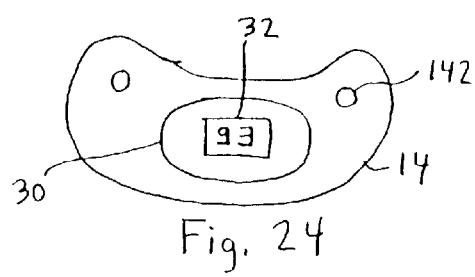

FIG. 24 illustrates a rear view of the alternative embodiment of the invention illustrated in FIG. 23.

Figure 25:
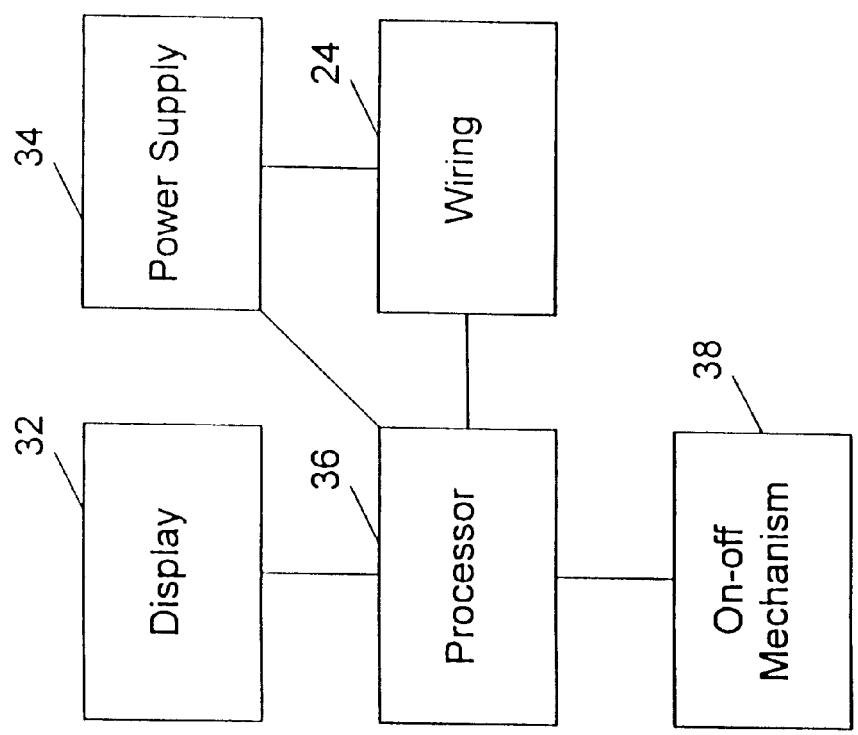

FIG. 25 depicts a block diagram for an alternative embodiment of the invention illustrated in FIGS. 23 and 24.

Figure 26:
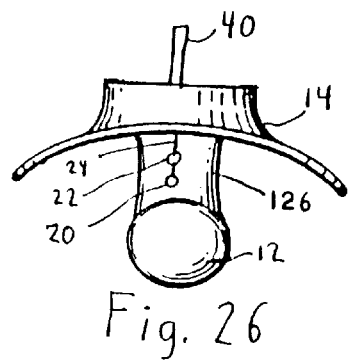

FIG. 26 illustrates a top view of another alternative embodiment of the invention.

Figure 27:
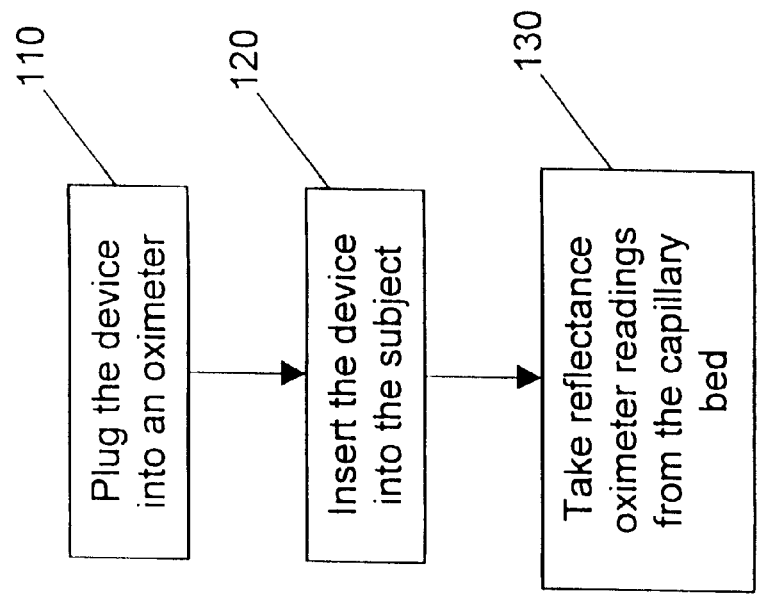

FIG. 27 depicts a flowchart illustrating the steps for performing the preferred embodiment.

V. DETAILED DESCRIPTION OF THE INVENTION

FIGS. 1–18 illustrate a preferred embodiment and alternative component arrangements of the pacifier oximeter sensor assembly. The assembly preferably includes a pacifier 10, pulse oximeter sensor elements 20, 22, and wiring 24.

The pacifier 10 preferably includes a nipple (or baglet) 12 and a shield (or guard) 14. The nipple 12 may be a variety of shapes in addition to those shown in FIGS. 1–18 that will allow the subject to apply a suction force to the nipple 12. Exemplary shapes for the nipple 12 include orthodontic, bottle nipple, spherical, and thumb shaped. The nipple 12 preferably is a flexible material typically used to make pacifiers and baby bottle nipples such as polypropylene, polyvinyl chloride, silicones, epoxies, polyester, thermoplastics, rubber, or similar flexible material. Preferably, the material used to make the nipple 12 will be at least partially translucent to allow light to pass through in the area of the pulse oximeter sensor elements 20, 22. Preferably, the nipple 12 will have an inner cavity 124 formed as a void in the nipple material 122. However, the nipple 12 may be solid or filled with a flexible material to increase the protection of the pulse oximeter sensor elements 20, 22 and wiring 24.

Figure 1:
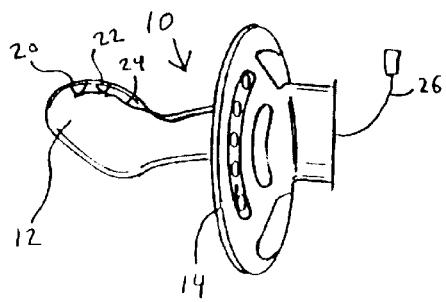
FIG. 1 depicts a side view of the preferred embodiment of the invention.
Figure 2:
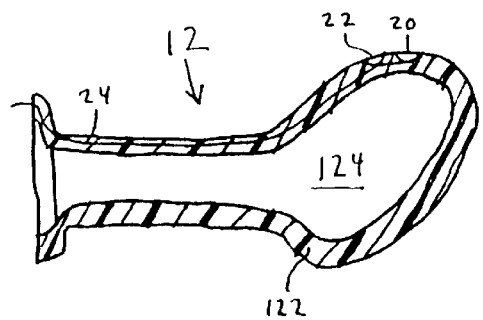
FIG. 2 illustrates a side cross-section of a nipple of the preferred embodiment of the invention.
Figure 3:
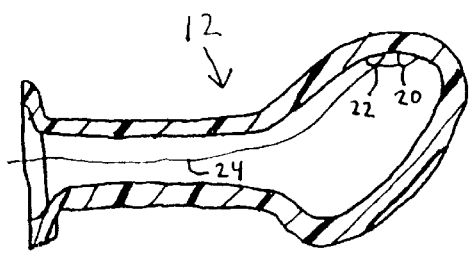
FIGS. 3–10 depict side cross-sections of a nipple to illustrate various alternative placements and arrangements of pulse oximeter elements according to the invention.
Figure 4:
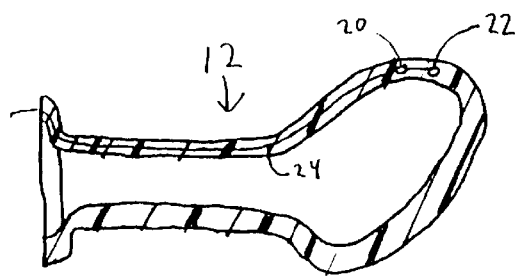
Figure 5:
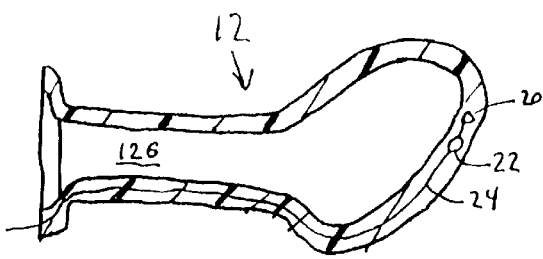
Figure 6:
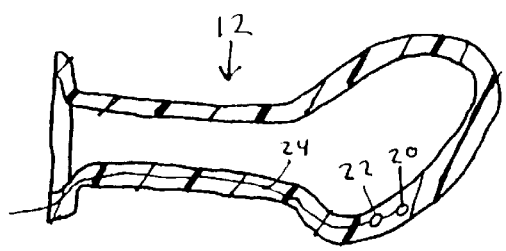
Figure 7:
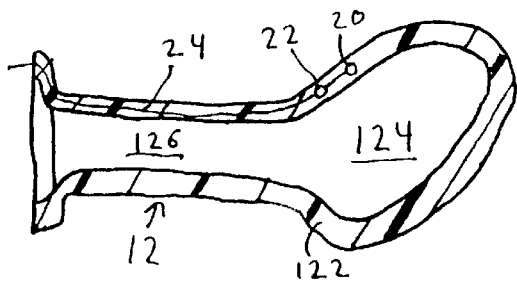
Figure 8:
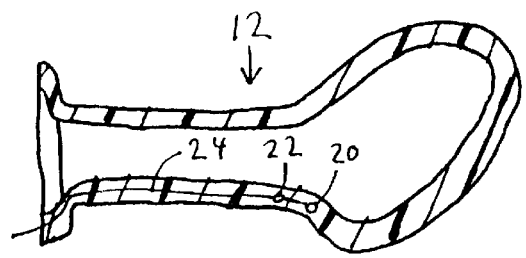
Figure 9:
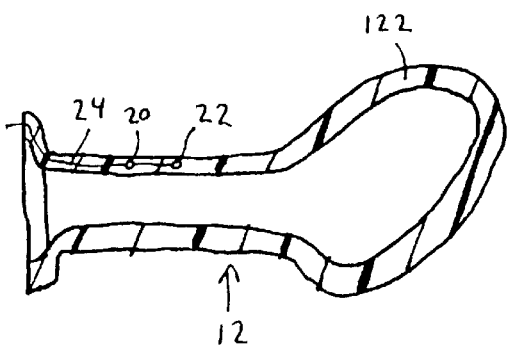
Figure 10:
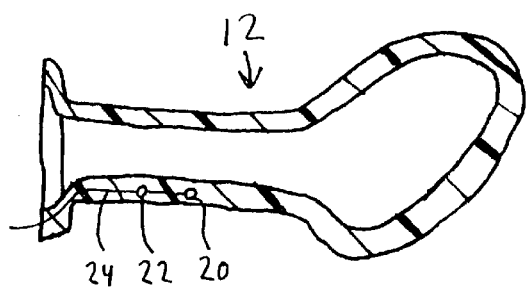
Figure 11:
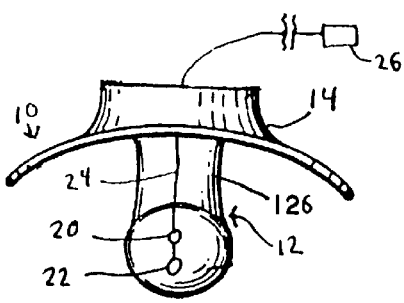
FIGS. 11–16 illustrate top views of various alternative placements and arrangements of the pulse oximeter elements according to the invention.
Figure 12:
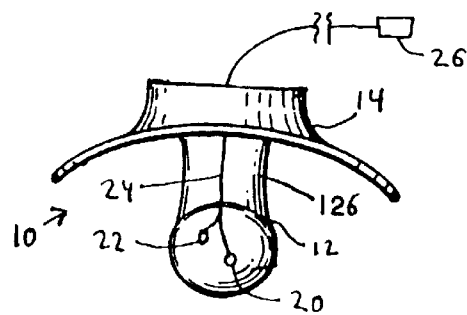
Figure 13:
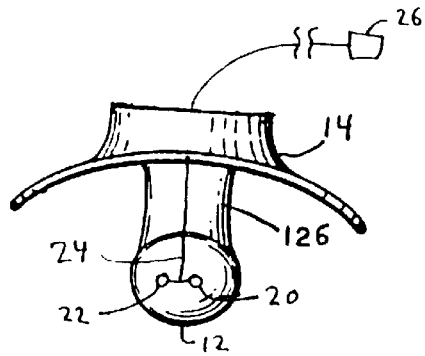
Figure 14:
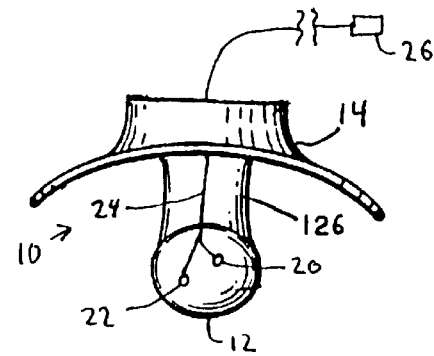
Figure 15:
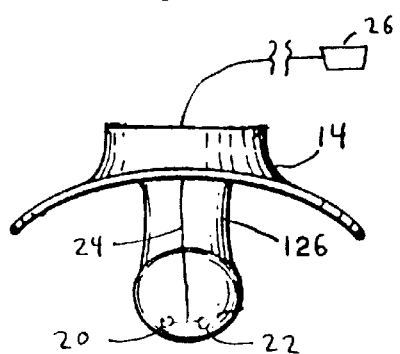
Figure 16:
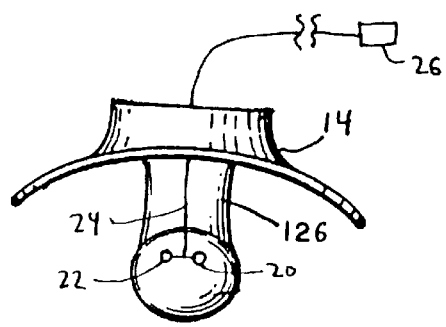

The pulse oximeter sensor elements 20, 22 preferably are within the material 122 making up the nipple 12 to reduce the impact of the material 122 on the transmission of light through the material 122. However, the pulse oximeter sensor elements 20, 22 may be nested within the nipple material 122 as shown, for example, in FIG. 4 or the pulse oximeter sensor elements 20, 22 may abut the nipple material 122 on the inner cavity surface as shown, for example, in FIG. 3. The pulse oximeter sensor elements 20, 22 preferably will be placed in a position to transmit light and receive backscattered light from a capillary bed within the oral cavity of the subject as illustrated, for example, in FIGS. 17 and 18. The preferred locations are along the top of the nipple 12 (FIGS. 2–4), at the tip of the nipple 12 (FIG. 5), and along the bottom of the nipple 12 (FIG. 6). Also, the pulse oximeter elements 20, 22 may be located in and/or along the nipple shank 126 as illustrated, for example, in FIGS. 7–10.

Preferably, the pulse oximeter sensor elements include a light source 20 and a light detector 22. The placement and location of the light source 20 and the light detector 22 depicted in FIGS. 1–18 may be switched with respect to each other. Furthermore, the light source 20 and the light detector 22 may be in a variety of exemplary spatial locations relative to each other as shown, for example, in FIGS. 11–16. Although FIGS. 11–16 illustrated the pulse oximeter sensor elements 20, 22 on the top of the nipple 12, these elements may have similar spatial locations on other portions of the nipple 12 such as the tip, bottom, and along the shank 126.

The light source 20 preferably emits at least two frequencies of light in the red region, for example with a wavelength of 660 nm, and in the infrared region, for example with a wavelength of 940 nm, preferably in response to a signal from a spectrophotometer, other similar oximeter monitoring devices or multiparameter patient monitoring systems that provide oximetry readings. The light source 20 preferably is one or more of the following: two light emitters such as light emitting diodes (LED), a bispectral emitter, a dual spectral emitter, a photoemitter, or a semiconductor die. However, any light source that facilitates reflectance pulse oximetry may be employed. Typically, the two emitter arrangement will include a red LED around or at 660 nm and a near-infrared LED emitting in the range of 890 to 950 nm and more particularly at about 940 nm. The light source 20 may emit light having a bandwidth, for example, in the range of 20 to 50 nm.

Preferably, the light detector 22 detects light emitted by the light source 20. Signals representing the detected light are transmitted by the light detector 22 to a spectrophotometer, an oximeter monitoring device or a multiparameter patient monitoring system that provides oximetry readings by discriminating between the relative intensity of these emissions and provides an index as to the degree of oxygen saturation of hemoglobin in blood. Preferably, the light detector 22 may be one of the following: a photoelectric receiver, a photodetector, or a semiconductor die.

The wiring 24 preferably includes conductive lines and contact electrodes. The wiring 24 preferably is embedded within the nipple material 122, or passes through the nipple cavity 124, or some combination of these two. An external cord 26 preferably is insulated and connects to the wiring 24 at a proximal end of the pacifier 126 so that the external cord 26 is outside of the oral cavity of the subject. The external cord 26 preferably includes a standard plug design to interface with a pulse oximetry spectrophotometer, a pulse monitor such as a plethysmograph, or other external device. Alternatively, the external cord 26 may be a jack to connect to a reusable cable such as the cable sold with the Nellcor® OxiCliq® systems (Mallinckrodt, Inc., St. Louis, Mo., U.S.A.).

Figure 19:
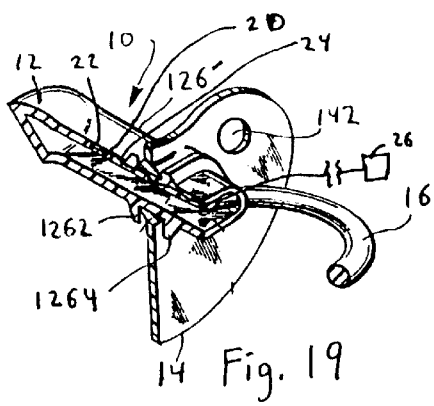
FIGS. 19 and 20 illustrate cross-sections of examples of attaching the nipple to the shield for the preferred embodiment of the invention.

The nipple 12 preferably is attached or mounted to the shield 14. An example of one type of mounting is integrally forming the nipple 12 with the shield 14, for example by mechanically coupling the nipple 12 to the shield 14. Another mounting arrangement, as illustrated in FIG. 19, is to have the nipple 12 include a shank 126' with two integral spaced collars 1262, 1264 to form a channel to receive the shield 14. Preferably, the shield 14 is at or near the proximal end of the shank 126'. Preferably to prevent the shield 14 from being pulled off the shank 126', a handle 16 is looped through the shank 126' as illustrated in FIG. 19.

Figure 20:
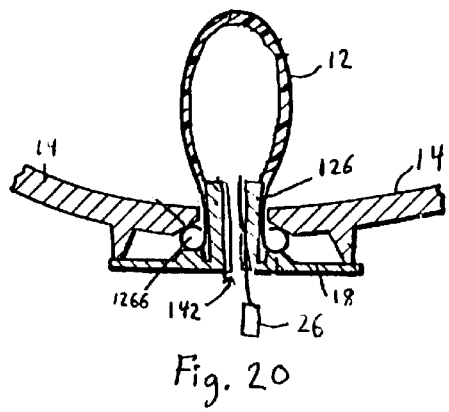
Figure 17:
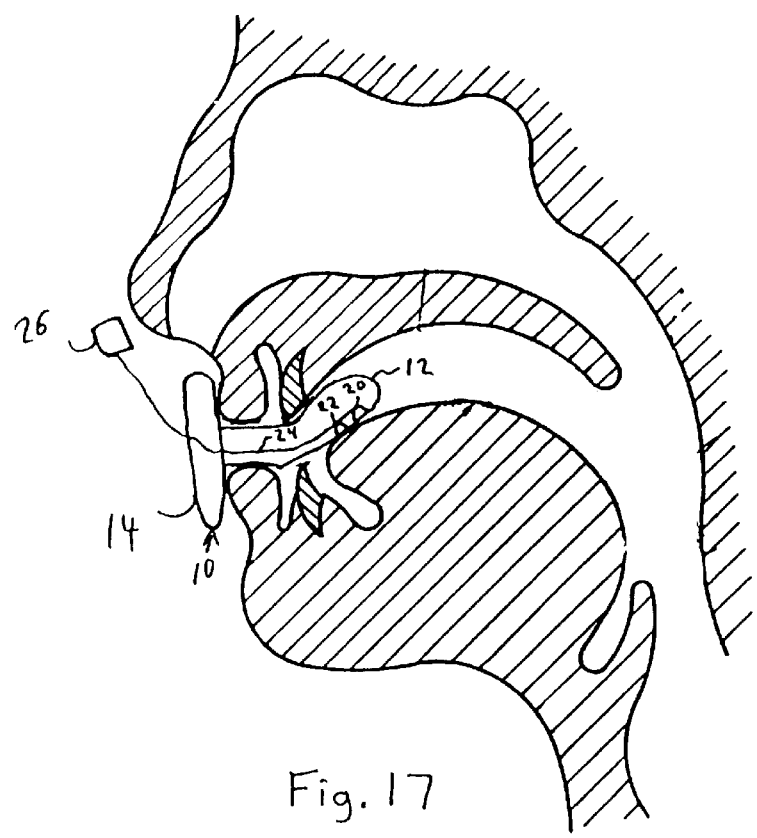
FIGS. 17 and 18 depict the invention in use in a subject.
Figure 18:
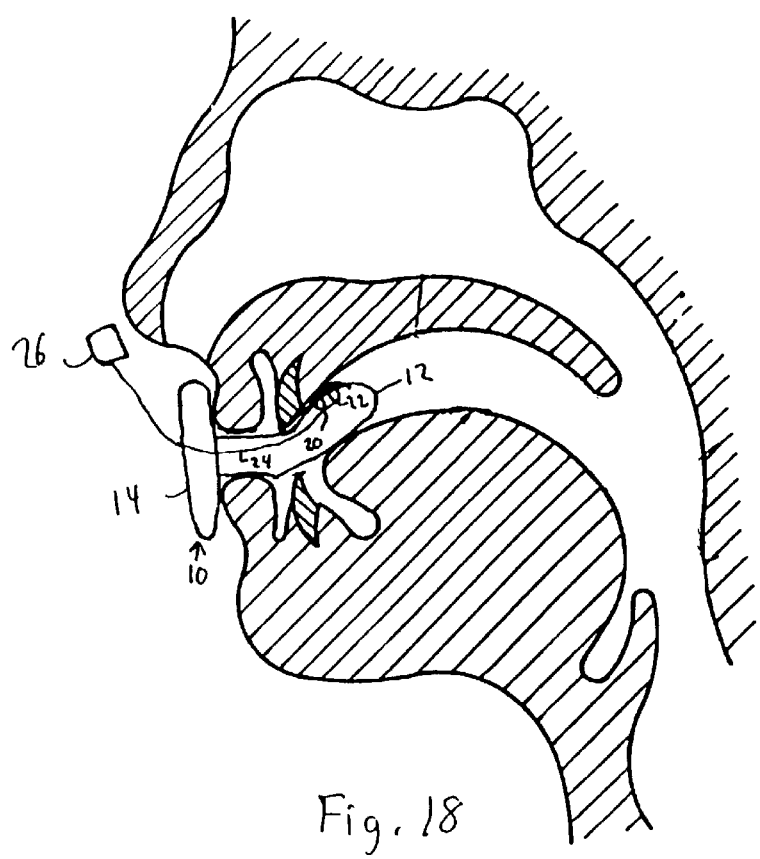

Another example of attaching the nipple 12 to the shield 14 is illustrated in FIG. 20. The shield 14 includes an opening for the nipple shank 126 to pass through preferably such that a rim or section of rolled up material 1266 is located on the proximal side of the shield 14. A plug 18 is inserted into the shield opening 142 to hold the nipple shank 126 in place with respect to the shield 14. More preferably, the plug 18 will include a securing mechanism that is compressed as it travels through the shield opening 142 and then expands on the distal side of the shield 14 to secure the plug 18 in place and hold the nipple 12 securely to the shield 14.

The shield 14 preferably is curved or bowed to form fit to the average baby's face. The shield 14 may be any shape that prevents it from being pulled into the subject's mouth from the suction force placed upon the nipple 12 by the subject. More preferably, the shield 14 will be shaped or include a reference indicator such that the top of the pacifier 10 can be readily determined by looking at the shield 14. In an alternative embodiment, the shield 14 preferably includes a plurality of holes (or relief openings) 142 to allow for spit to be discharged without interference from the pacifier 10 as illustrated, for example, in FIGS. 21(a), 23, and 24. FIG. 21(b) illustrates a relief opening 142' that allows insertion of a catheter such as an endotracheal tube. A further alternative is for the shield to include a mesh pattern over at least a portion of it. Another alternative embodiment adds a. ring (or annular or other shaped handle) 16 on the opposite side of the shield 14 from the nipple 12 as illustrated in FIGS. 21(a) and 22 that may attach to either the shield 14 or the nipple 12. Preferably, the ring is hinged, collapsible, and/or flexible.

An alternative embodiment of the invention is the placement of the oximeter signal processing device within a housing 30 extending from the shield 14 on the side opposite the nipple 12 as illustrated, for example, in FIGS. 23 and 24. The oximeter signal processing device preferably is a miniature spectrophotometer. The oximeter signal processing device preferably will include a display 32, a power supply (such as a battery) 34, and a processor 36 to perform calculations and to drive the display 32, and an on-off button (or switch/mechanism) 38 as illustrated in FIG. 25.

The display 32 preferably will show the blood oxygenation level of the subject as illustrated in FIG. 24. More preferably, the display 32 is a digital display. The processor 36 preferably will connect to the wiring 24 running from the pulse oximeter sensor elements 20, 22, calculate the blood oxygenation level, and drive both the display 32 and the light source 20. The processor 36 preferably is a circuit that includes either an analog circuit or an integrated circuit, which is either hardwired or programmed. Preferably, the display 32, the power supply 34, the processor 36 will reside on a printed circuit board that includes appropriate circuitry and provides a connection to wiring 24.

Another alternative embodiment of the invention is that the light source 20 and the light detector 22 may be in wireless communication with the external device instead of connected with the external cord 26 as illustrated in FIG. 26 as a rod (or antenna or transmitter) 40. Alternatively, the antenna 40 may take the shape as a handle 16 similar to the one illustrated, for example, in FIGS. 21 and 22 without the external cord 26. Preferably, the wireless communication will occur through an antenna 40 extending away from the pacifier 10. The transmitter may be incorporated within the antenna 40 or some other housing incorporated into the shield 14. Preferably, the antenna 40 will be sufficiently sturdy to withstand tugging and being played with during use by the subject. This alternative embodiment also preferably includes a power source such as a battery to power all of the electrical components. The power source preferably is located within the shield, a housing, or as part of the antenna 40.

A further alternative embodiment of the invention is to provide a bite block on the distal side of the shield 14 between the shield 14 and the nipple 12. The bite block may be an extension of the shield material or a hardened nipple shank 126. The flexible nipple 12 preferably is attached to the bite block. Preferably, the bite block will provide a passageway through which the wiring 24 may pass through. The shield 14 and nipple 12 preferably would be shaped such that multiple catheters would have space to enter the oral cavity, for example, for suction and supplying oxygen. This alternative embodiment preferably would be for use during surgery of a variety of subjects other than infants and young children.

The device may be a retrofit of current pacifiers by inserting the pulse oximeter sensor elements from a disposable pulse oximeter like the Nellcor® Oxisensor® II oximeters (Mallinckrodt, Inc., St. Louis, Mo., U.S.A.) by stripping away the packaging and adhesive strip. The ring attached to must pacifiers would be removed leaving access to the interior cavity of the nipple into which the pulse oximeter sensor elements would be inserted such that they faced in the same general direction. The ring then would be reattached.

In accordance with the present invention, there is a method to take oximeter readings from different sites within a subject, which may be either human or animal, for the purposes of determining the amount of oxygen within the blood of the subject. The oximeter readings are accomplished using reflectance oximetry from capillary beds that are readily accessible within the subject. The capillary beds include, for example, the hard palate, the soft palate, the superior lingual surface, the inferior lingual surface, the gingivae, the mouth floor, the buccal surface, and any other surface within the oral cavity. Each of these capillary beds is accessible through the oral cavity, which extends from the lips to the oral portion of the pharynx, i.e., pars oralis.

FIG. 27 illustrates a flowchart showing the steps for taking oximeter readings pursuant. to the present invention. In the first step 110, which may actually occur at a later point but no later then the initiation of taking pulse oximeter readings, the pulse oximeter sensor elements are connected to an oximeter device such as a spectrophotometer. In step 120, the pacifier 10 is inserted into the subject through the mouth. The placement of the pacifier 10 with a pulse oximeter sensor is illustrated, for example, in FIGS. 17 and 18. In step 130, reflectance pulse oximeter readings are taken from the relevant capillary bed. While taking the pulse oximeter readings, the pulse oximeter sensor elements preferably remain in contact with the relevant capillary bed to continue the flow of accurate oximeter readings.

The method according to the invention may be used in a variety of surgical, anesthetic, critical care procedures or situations that include patients that are awake, sedated or recovering from general anesthesia.

The method of taking pulse oximeter readings from different surfaces within a patient has been submitted to actual testing in the below-described population and according to the following protocols.

Reflectance Oximetry from the Buccal Surface

The first protocol involved taking readings from the buccal surface. Nine patients were monitored via buccal reflectance pulse oximetry over 20 consecutive surgical procedures, which procedures consisted of burn excision and grafting. Patients ranged in age from 23 to 56 years (Mean=264.8, Standard Deviation (SD)=11.2) and ranged from 17 to 75 percent total body surface area (%TBSA) burned (Mean=274.3%, SD=28.9). Each patient received from one to eight operations (Mean=4.01).

Five of these nine patients arrived at the operating room intubated for all of the operations in this study. Four patients were induced and intubated in a standard fashion for all surgical procedures.

A Nellcor® Oxisensor® II D-25 was placed intraoraly between the lower teeth and the left or right buccal surface of the cheek and lip, with the bispectral emitter and detector facing the buccal surface. This pulse oximeter sensor orientation was used for the duration of each case. In addition, a similar disposable oximetric probe was placed on a peripheral digit in the commonly accepted transillumination configuration. At five minute intervals throughout the case, values for both oximetric probes were coded on the anesthesia record.

The differences between the peripheral and buccal $SpO_2$ (oxygen saturation of hemoglobin) values were insignificant by t-tests for correlated means. Concordance rates as percent agreements were calculated for all cases. Average percent agreement was 84% ranging from 25% to 100%. Three of the 20 samples had percent agreements less than 91%. In each of these cases, the peripheral pulse oximeter sensor appears to have failed, in two cases secondary to sepsis, and in another secondary to peripheral vasoconstriction in the face of a norepinepherine infusion. Buccal $SpO_2$ readings in all three cases continued to be 97% or greater.

This data suggests that buccal reflectance oximetry is a simple, accurate means of monitoring arterial oxygen saturation in the severely burned patient where oximetric monitoring presents a challenge. Given that central oximetry has been shown in numerous studies to be more rapidly responsive to oxygen saturation variability than peripheral oximetry, as well as more directly reflective of central oxygen saturation, there are few drawbacks and considerable benefit from this method. Indeed, in the three examples in this study where percent agreements were low, the peripheral oximetric probes were returning apparently erratic and/or generally low values while buccal oximetric readings remained at 97% or higher. All three of these patients had peripheral vascular compromise secondary to sepsis and/or a vasoconstricting agent (norepinepherine infusion).

It may appear from the study results, at first blush, that a full range of $SpO_2$ values was not tested and that the continuously high $SpO_2$ readings are spurious to the technique. On the contrary, in order to obtain a $SpO_2$ value greater or less than 85% a very specific set of relationships must be present relative to the bispectral emitter and light sensing oximetric elements. Thus, spuriously high values in particular do not consistently occur. High $SpO_2$ values require the presence of saturated hemoglobin.

Posterior Pharvngeal Reflectance Oximetry

The second protocol involved comparing posterior pharyngeal reflectance pulse oximetry to conventional peripheral transillumination pulse oximetry in difficult to monitor burn patients. Eight patients' records were reviewed over fourteen consecutive surgical procedures, all consisting of excision and grafting. Patients ranged in age from 9 to 43 years and ranged from 14.5% to 77.5% TBSA burned (Mean=30.4, SD=22. 1). The number of operations per patient ranged from one to four.

A Nellcor® Oxisensor® II pulse oximeter probe was placed in the distal lumen of an appropriately sized oropharyngeal airway with sensor and emitter facing the posterior pharynx. A similar probe was placed on a peripheral digit as a transilluminating pulse oximeter. $SpO_2$ values were noted at five-minute intervals. Concordance statistics as well as a t-test for correlated means were calculated between the simultaneously obtained $SpO_2$ values.

The mean differences between pharyngeal reflectance and peripheral digital transillumination $SpO_2$ values were insignificant for all cases. Concordance statistics were as follows: 0.75 (n=1) and 1.0 (n=12).

Given the near perfect concordance statistics in this study, this data suggests that posterior pharyngeal reflectance oximetry is a simple, highly accurate means of monitoring arterial oxygen saturation in the severely burned patient where oximetric monitoring presents a challenge.

Lingual Surface Reflectance Oximetry

The third protocol involved taking readings from the lingual surface. Data was reviewed for eight difficult to monitor patients who were monitored via lingual reflectance pulse oximetry over twenty-five consecutive surgical procedures, all consisting of burn excision and grafting. Patients ranged in age from 26 to 57 years (Mean=36.0, SD=10.3). Patients ranged from 20% to 92% TBSA burned (Mean=66.75%, SD=26.42). Number of operations per patient ranged from one to five (Mean=3.13, SD=1.55). Six of these eight patients arrived at the operating room intubated for all of the operations in this study. Two patients were induced and intubated in a standard fashion.

In each case, a Nellcor® Oxisensor® D II D-25 was centered flat on the superior lingual surface with the detector and the bispectral emitter facing the lingual surface. This pulse oximeter configuration was used for the duration of each case. When clinically indicated, an arterial blood gas (ABG) sample was drawn and the $SpO_2$ noted for clinical monitoring and prior to transfusion in every case. All had multiple ABG's drawn and all patients were transfused. The ABG $SaO_2$ (oxygen saturation of arterial blood) was noted in each case.

Descriptive statistics and a concordance rate as well as a t-test for correlated means were calculated between the simultaneously obtained $SpO_2$ and $SaO_2$ values. The difference between the $SpO_2$ and $SaO_2$ values was insignificant by t-test for correlated means (t=1.25, df=24, NS). Upon inspection, the means were very close and the standard deviations were very small, as were the SEM's, all suggesting very little difference or variability between these two measures of oxygen saturation. A concordance rate of 92% was calculated (+1.5%) showing a high degree of relationship between lingual and ABG $SaO_2$.

This data suggests that lingual reflectance oximetry is a simple, accurate means of monitoring arterial oxygen saturation in the severely burned patient where oximetric monitoring presents a challenge. An existing disposable pulse oximeter sensor was utilized in this study saving the cost of specially designed equipment. Given that central oximetry has been shown to be more rapidly responsive to oxygen saturation variability than peripheral oximetry, there are few drawbacks and considerable benefit from this method.

VI. INDUSTRIAL APPLICABILITY

The invention is particularly useful for monitoring the blood oxygen content of a subject, more particularity a child or infant. The invention is also useful when other sites are not available on the patient such as a patient with severe burns covering most of their body or a restless child who is prone to remove attached oximeters to fingers and other body parts. The invention may be used by hospital personnel, emergency medical crews, in-home medical personnel, laboratory and veterinary personnel and battlefield medical personnel.

Those skilled in the art will appreciate that various adaptations and modifications of the above-described devices and steps can be configured without departing from the scope and spirit of the their use in the method. Therefore, it is to be understood that, within the scope of the appended claims, the method may be practiced and arranged other than as specifically described herein. Furthermore, the above-described embodiments may be used in a variety of combinations.

We claim:

1. An oximeter sensor comprising:
   a nipple,
   a shield connected to said nipple, and
   oximeter sensor elements in said nipple; and
   wherein said oximeter sensor elements are arranged to perform reflectance pulse oximetry.

2. The device as recited in claim 1, wherein said oximeter sensor elements include:
   means for transmitting light at an intraoral tissue, and
   means for receiving light reflected from the intraoral tissue.

3. The device as recited in claim 2, wherein said means for transmitting and said means for receiving are embedded in said nipple.

4. The device as recited in claim 2, wherein
   said nipple includes an inner cavity, and
   said means for transmitting and said means for receiving are disposed in the inner cavity of said nipple.

5. The device as recited in claim 1, wherein said oximeter sensor elements include:
   at least one light source, and
   at least one light detector in communication with said at least one light source.

6. The device as recited in claim 5, wherein said light source includes one of at least one light emitter, a bispectral emitter, a dual spectral emitter, at least one photoemitter, at least one photodiode, at least one light emitting diode, and a semiconductor die.

7. The device as recited in claim 6, wherein said light detector includes one of a photoelectric receiver, a photodetector, a photodiode receiver, and a semiconductor die.

8. The device as recited in claim 6, wherein
   said nipple includes an inner cavity, and
   said light source and said light detector are disposed in the inner cavity of said nipple.

9. The device as recited in claim 7, wherein said light source and said light detector are embedded within said nipple.

10. The device as recited in claim 5, further comprising:
    a transmitter,
    a power source, and
    wiring connecting said light source, said light detector, and said transmitter to said power source, said wiring connecting said light source and said light detector to said transmitter.

11. The device as recited in claim 5, wherein said light source and said light detector are disposed near a top of said nipple.

12. The device as recited in claim 5, wherein said light source and said light detector are disposed near a tip of said nipple.

13. The device as recited in claim 5, wherein said light source and said light detector are disposed near a bottom of said nipple.

14. The device as recited in claim 5, further comprising an oximeter device, said oximeter device includes:
    a display,
    a power supply connected to said display, and
    a processor connected to said power supply and said display, said processor is in communication with said light source and said light detector; and
    wherein said processor signals said light source to transmit light, and
    said processor receives at least one signal from said light detector representing light detected by said light detector.

15. A method for using the device recited in claim 1 comprising:
   connecting the device to an oximeter,
   inserting the device into a mouth of a subject, and
   taking reflectance pulse oximeter readings.

16. The device as recited in claim 1, further comprising a plug engaging said nipple and said shield such that at least a portion of said nipple is held in place between said plug and said shield.

17. The device as recited in claim 1, further comprising a bite block connecting said shield to said nipple.

18. An oximeter system comprising:
   a spectrometer, and
   a pacifier oximeter sensor having a nipple, a shield attached to said nipple, and pulse oximeter sensor elements within said nipple.

19. The oximeter system according to claim 18, wherein said pulse oximeter sensor elements include a light source and a light detector.

20. A pulse oximeter sensor comprising:
   means for restricting inward suction of the pulse oximeter sensor into a subject,
   means for performing reflectance pulse oximetry inside the subject, and
   means for housing said oximetry means.

* * * * *